United States Patent [19]

Arnold et al.

[11] Patent Number: 4,634,669

[45] Date of Patent: Jan. 6, 1987

[54] PROCESS AND DEVICE FOR THE DIFFERENTIATION OF PARTICLES IN A MEDIUM

[75] Inventors: William M. Arnold, Aachen; Ulrich Zimmermann, Hurtgenwald-Gey, both of Fed. Rep. of Germany

[73] Assignee: Kernforschungsanlage Jülich, Jülich, Fed. Rep. of Germany

[21] Appl. No.: 631,847

[22] Filed: Jul. 18, 1984

[30] Foreign Application Priority Data

Jul. 18, 1983 [DE]  Fed. Rep. of Germany ....... 3325860

[51] Int. Cl.⁴ .............................................. C12N 13/00
[52] U.S. Cl. ........................................ 435/173; 424/3; 435/4; 436/149; 436/151; 436/806
[58] Field of Search .................. 128/1.3; 424/3; 435/4, 435/173; 436/149, 151, 806

[56] References Cited

U.S. PATENT DOCUMENTS 3,418,500  12/1968  Davis .................................. 310/308

FOREIGN PATENT DOCUMENTS 1096280  6/1984  U.S.S.R. .............................. 435/173

OTHER PUBLICATIONS

Laboratory Equipment Digest, vol. 18, No. 10, (Oct. 1980), pp. 91–93.

*Primary Examiner*—Christine M. Nucker
*Assistant Examiner*—Stephen C. Wieder
*Attorney, Agent, or Firm*—Pahl, Lorusso & Loud

[57] ABSTRACT

Disclosed is a process and device for facilitating the differentiation of particles in a medium. The particles are exposed to a rotating electrical field of variable rotational frequency. By providing a means for adjusting the frequency of the rotating fields, the particles can be caused to rotate in different directions thereby facilitating differentiation of particles belonging to different groups of particles. An apparatus for implementing this process includes at least three electrodes which are arranged so as to form a space therebetween. A device for producing a rotating field of variable rotational frequency is connected to the electrodes.

4 Claims, 1 Drawing Figure

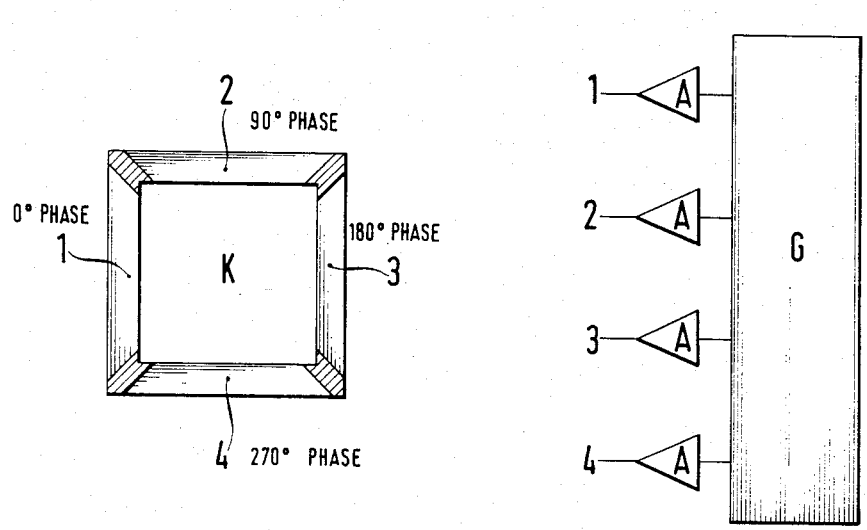

PROCESS AND DEVICE FOR THE DIFFERENTIATION OF PARTICLES IN A MEDIUM

BACKGROUND OF THE INVENTION

This invention concerns a process for the differentiation of particles (especially cells), belonging to at least two groups of particles in a medium, which can rotate around an axis of rotation parallel to the axis of rotation of a rotating electrical field.

It is known from Z. Naturforsch. 37 c, 908–915 (1982), "Rotating-Field-Induced Rotation and Measurement of the Membrane Capacitance of Single Mesophyll Cells of Avena sativa", W. M. Arnold and U. Zimmermann, that individual cells, protoplasts in this case, can be brought into rotation in a rotating electrical field which is produced, for example, by four electrodes displaced by 90° from one another. It is also known that individual cells of a specific species of cells can be placed in maximum rotational speed at a specific frequency of the rotating field (the so-called characteristic frequency).

When using the known process, cells, for which different characteristic rotational frequencies are determined for the particular maximum rotational speed, can be differentiated from one another by adjusting the frequency of the rotating field to the characteristic frequency for one group of cells. The different cells can then be differentiated from one another by their different rotational speed. However, with this procedure in a specific case, the differentiation on the basis of the different rotational speed can be truly difficult, so that only a trained eye is able to recognize the difference.

It is therefore a principal object of the present invention to provide a process for facilitating the differentiation of particles on the basis of their rotational behavior for an operator.

Another object of the present invention is to provide a process for the differentiation of particles of a nonbiological nature.

A further object of the present invention is to provide a device for facilitating the differentiation of particles on the basis of the rotational behavior.

SUMMARY OF THE INVENTION

According to the present invention, a process and device for facilitating the differentiation of particles is provided in which the particles are exposed to a rotating electrical field of variable rotational frequency. The frequency of the rotating field is adjusted to a frequency at which the particles to be differentiated rotate in different directions.

For the implementation of the process pursuant to the invention, an apparatus is provided in which at least three electrodes formng an intermediate space between themselves for a chamber containing the cells, or forming a container, or extending into the chamber provided to hold the cells, are arranged in such a way that the chamber or container space is exposed to a rotating electrical field produced by the electrodes. The apparatus also includes a device, which can be connected to the electrodes, for producing a rotating field of variable rotational frequency. Appropriately, the intensity of the rotating field is also variable, but is should be within such a range that electrical field strengths of approximately 1 to 1000 V/cm are produced in the chamber. The frequency range should lie within the region between 1 Hz and 1 GHz. In many applications, however, a range of 1 Hz to 500 kHz suffices.

These and other features and objects of the present invention will be more fully understood from the following detailed description which should be read in light of the accompanying drawings.

BRIEF DESCRIPTION OF THE DRAWING

One form of embodiment of the device pursuant to the invention is illustrated schematically in the drawing and is described in detail below.

DETAILED DESCRIPTION OF THE PREFERRED EMBODIMENTS

The process pursuant to the invention is based on the determination that particles, and also cells, rotate in a rotating electrical field not only in the same direction of rotation as the rotating electrical field, but depending on their specific properties which determine their rotational behavior, they can also sometimes be set into rotation with a direction of rotation opposite to the direction of rotation of the rotating electrical field.

It has been found that there are a large number of particles, for example cells of Saccharomyces cerevisiae (Strain 93) which indeed rotate in a broad frequency range of the rotating field, but not in the same direction of rotation as the rotating field over the entire frequency range. Since this rotational behavior, i.e., the position of the regions with different direction of rotation, depends on the specific properties of the particles, it is also possible simply to differentiate, from one another, particles of two groups, for example, which have a different rotational behavior of the aforementioned type. To this end, it is merely necessary to vary the frequency of the rotating field until the particles to be differentiated rotate in opposte directions.

The process pursuant to the invention is applicable to a broad area of technology. Where it is desired to differentiate particles of a powder, optical methods, such as study under the microscope, may not be adequate. Thus, it may be of interest, for example, to differentiate $BaTiO_3$ particles from $TiO_2$ particles which are present as a result of the manufacturing process for $BaTiO_3$, and to be able to make an estimate of the percentage proportion of $TiO_2$ particles in a batch. This is readily possible because $BaTiO_3$ particles rotate in a direction opposite to that of $TiO_2$ particles over a broad frequency range under the action of an electrical field.

In the biological, pharmacological, and medical area it is of interest to differentiate cells from one another. For example, when cells have a cell wall, such as plant cells, yeast cells, and bacteria, and given an equal size of the cells, the cells cannot be differentiated under the microscope in spite of other differences. Thus, for example, cells of the same species and genus having a cell wall also cannot be differentiated under the microscope when their membrane has been damaged by detergents, environmental polllutants such as heavy metals, and the like. If the damage in the membrane of the cells is not too slight, damaged cells differ in specific frequency regions by rotation in a direction of rotation opposite to the direction of rotation of undamaged cells. The damaged cells can therefore be differentiated from the undamaged cells on the basis of their different rotational behavior. Living cells can also be differentiated from dead cells of the same species, for example, by means of their rotational behavior.

The rotational behavior of the particles, such as for a specific species of cell, actually depends on other parameters, such as the environmental conditions for the particles, the conductivity of the medium in which the particles are located, and the temperature of the medium. However, only the different rotational behavior of the particles to be differentiated is involved in a differentiation measurement, with otherwise identical environmental conditions. The conductivity of the medium, which appropriately lies within a range from 5 to 500 $\mu$S/cm, especially 5 to 50 $\mu$S/cm, is therefore of only subordinate importance for the differentiation of the particles themselves. In the case of cells to be differentiated, the temperature of the medium is primarily adjusted so that the cell functions are not impaired and the cells are not damaged.

In carrying out the process pursuant to the invention, an intensity is chosen which lies below the electrical breakdown voltage for cells to be treated. It has been found that it is also appropriate for the electrical voltages producing the rotating field to be sinusoidal. However, it is also possible to produce the rotating field by square-wave voltages or by pulsed voltages or voltages of another form.

The apparatus according to the present invention includes four electrodes which are positioned on a base plate of electrically nonconductive material, not shown in the drawing, so that they form the lateral walls of the chamber K provided to hold the cells. The electrodes are cemented to one another and to the base plate by means of an electrically insulating ashesive. The electrode length and thus the length of the lateral walls of the chamber is 1 mm, and the height of the electrodes is 0.2 mm. The rectangular chamber K open at the top thus has the lateral dimension of 1 mm and the height of 0.2 mm. The electrodes consisting of platinum foil are connected to the amplifiers A of the generator G in the order shown in the drawing. The voltages transmitted by the amplifiers, as also seen in the drawing, are shifted in phase by 90° in each case, whereby a rotating electrical field is produced in the chamber.

EXAMPLE 1

Differentiation of nonbiological particles

A particle mixture consisting of $BaTiO_3$ and $TiO_2$ (the average diameter of the particles was 2 $\mu$m) was washed 5 times in distilled water and then placed in water which contained traces of NaCl (conductivity 2.6 $\mu$S/cm, temperature 20° C.).

Approximately 10 $\mu$l of the solution containing the mixture of particles was placed in the rotation chamber. The particles could be differentiated in a frequency range of 5 to 150 kHz by their different directions of rotation. While the $BaTiO_3$ particles rotated with the rotating electrical field, the $TiO_2$ particles rotated opposite to the direction of rotation of the electrical field.

It should be noted that $BaTiO_3$ has a dielectric constant of 2000, while $TiO_2$, on the other hand, has a dielectric constant of approximately 100.

EXAMPLE 2

Differentiation of nonbiological particles

Corresponding to Example 1, a mixture of $BaTiO_3$ and $TiO_3$ particles was studied. The conductivity of the solution containing the mixture was 5.2 $\mu$S/cm.

In the frequency range from 10 to 300 kHz, the two types of particles rotated in opposite directions of rotation.

EXAMPLE 3

Differentiation of living and dead yeast cells

Cells of *Saccharomyces cerevisiae* (Strain 93) from a nutrient medium were placed in distilled water. Some of the yeast cells were heated for 5 minutes at 85° C. They were then centrifuged and washed.

A fraction of the heated yeast cells was mixed with the untreated yeast cells. No difference could be seen under the microscope. The mixture was placed in a solution whose conductivity was 2 $\mu$S/cm. and whose temperature ws 20° C. Approximately 10 $\mu$l of the solution containing the mixture of cells were placed in the rotation chamber.

The cells rotated in a broad frequency range, although in a different direction of rotation at approximately 100 kHz. In this case, the living cells rotated opposite to the direction of rotation and the dead cells with the direction of rotation of the electrical field.

EXAMPLE 4

Differentiation of cells damaged by a detergent from undamaged cells.

Cells of *Saccharomyces cerevisiae* (Strain 93) were placed in a starting solution consisting of distilled water. Some of these were placed for 1 hour in a solution which contained 0.09% HDTAB (hexadecyltrimethylammonium bromide). The cells were then centrifuged and washed four times in distilled water. A mixture of treated and untreated cells was prepared (the conductivity of the solution was 2 $\mu$S/cm, and the temperature was 20° C.). The cells could not be differentiated under the microscope.

A study in the rotation chamber showed a different rotational behavior of the two groups of cells. The cells could be differentiated even at 20 Hz, since the undamaged cells rotated with the rotating field, and the damaged cells did not rotate.

At 40 kHz, the cells rotated with different direction of rotation, with the damaged cells rotating with the rotating field and the undamaged cells rotating opposite to the direction of the rotating field.

EXAMPLE 5

Differentiation of cells damaged by environmental pollutant from undamaged cells Some of the cells from the starting solution specified in Example 4 were placed for 1 hour in a solution which contained 100 ppm of $HgCl_2$. After centrifuging the cells and washing them four times, a mixture of treated and untreated cells were again prepared. The conductivity of the solution containing the mixture was 2 $\mu$S/cm, and the temperature was 20° C. No difference could be seen under the microscope between the cells in the mixture.

A study in the rotation chamber showed a different rotational behavior for each of the two groups of cells. The cells could be differentiated even at 20 Hz, since the undamaged cells rotated with the rotating field, and the damaged cells did not rotate.

At 50 kHz, the cells rotated with a different direction of rotation, with the damaged cells rotating with the rotating field and the undamaged cells rotating opposite to the direction of the rotating field.

EXAMPLE 6

Differentiation of yeast cells of two different genera

A mixture of yeast cells *Saccharomyces cerevisiae* (Strain 93) and Hansenula II (unknown species) was prepared. The two groups of cells could not easily be differentiated from one another under a microscope.

The mixture of cells was placed in distilled water (conductivity 2 μS/cm, temperature 20° C.). The cells could be differentiated from one another by their rotational behavior. At 30 kHz, the cells of *Saccharomyces cerevisiae* (Strain 93) rotated opposite to the direction of rotation of the electrical field, while conversely, the cells Hansenula II rotated slowly in the direction of rotation of the rotating electrical field.

The foregoing invention has been described with reference to its preferred embodiments and a number of non-limiting examples. Although variations and modifications will occur to those skilled in the art, it is intended that such variations and modifications fall within the scope of the appended claims.

What is claimed is:

1. A process for the differentiation of particles belonging to at least two groups of particles in a medium, said particles being capable of rotating around an axis of rotation parallel to the axis of rotation of a rotating electrical field, comprising the steps of:

exposing the particles to a rotating electrical field of variable rotational frequency, adjusting the frequency of the rotating field to a frequency at which the particles to be differentiated rotate in different directions.

2. A process for differentiating particles belonging to at least two groups of particles in a medium, comprising the steps of:

providing at least three electrodes forming between themselves an intermediate space containing the cells, or forming a container, or extending into the chamber provided to hold the cells, said at least three electrodes being arranged in such a way that the chamber or container space may be exposed to a rotating electrical field produced by the electrodes, and providing means connected to the electrodes to produce a rotating field of variable rotational frequency, exposing the particles to a rotating electrical field of variable rotational frequency, adjusting the frequency of the rotating field to a frequency at which the particles to be differentiated rotate in different directions.

3. The process for differentiating particles of claim 2 further comprising the step of varying the intensity of the rotating field.

4. The process for differentiating particles of claim 2 wherein the voltages producing the rotating field are sinusoidal.

* * * * *